(12) United States Patent
Park et al.

(10) Patent No.: US 8,159,525 B2
(45) Date of Patent: Apr. 17, 2012

(54) PORTABLE MULTISPECTRAL IMAGING SYSTEMS

(75) Inventors: Bosoon Park, Bogart, CA (US); Michio Kise, Kennewick, WA (US); Kurt C. Lawrence, Watkinsville, GA (US); William Robert Windham, Watkinsville, WA (US)

(73) Assignee: The United States of America, as represented by the Secretary of Agriculture, Washington, DC (US)

( * ) Notice: Subject to any disclaimer, the term of this patent is extended or adjusted under 35 U.S.C. 154(b) by 388 days.

(21) Appl. No.: 12/456,022

(22) Filed: Jun. 9, 2009

(65) Prior Publication Data
US 2009/0309960 A1    Dec. 17, 2009

Related U.S. Application Data

(60) Provisional application No. 61/131,963, filed on Jun. 13, 2008.

(51) Int. Cl.
*H04N 13/02* (2006.01)

(52) U.S. Cl. .......................... 348/47; 348/139; 348/153
(58) Field of Classification Search .................... 348/47, 348/139, 153
See application file for complete search history.

(56) References Cited

U.S. PATENT DOCUMENTS

| | | | |
|---|---|---|---|
| 6,913,877 B1 * | 7/2005 | Chaplen et al. | 435/4 |
| 7,719,677 B2 * | 5/2010 | Rosengaus | 356/300 |
| 2003/0100824 A1 * | 5/2003 | Warren et al. | 600/407 |
| 2007/0015963 A1 * | 1/2007 | Fengler et al. | 600/109 |
| 2008/0088837 A1 * | 4/2008 | Gardner | 356/301 |
| 2008/0212089 A1 * | 9/2008 | Rosengaus | 356/300 |
| 2009/0021598 A1 * | 1/2009 | McLean et al. | 348/222.1 |

* cited by examiner

*Primary Examiner* — Phuoc Nguyen
(74) *Attorney, Agent, or Firm* — John D. Fado; Gail E. Poulos

(57) ABSTRACT

Multiport multispectral portable imaging systems having at least two cameras with charge-coupled device sensors, a front lens unit, at least two rear lens units, a beamsplitter, and at least two bandpass filters is used to detect contaminants on food.

5 Claims, 15 Drawing Sheets

(a)

(b)

(a)

(b)

(a)   (b)

PORTABLE MULTISPECTRAL IMAGING SYSTEMS

This application is a non-provisional application claiming benefit of provisional application 61/131,963 filed Jun. 13, 2008; which is herein incorporated by reference in its entirety.

BACKGROUND OF THE INVENTION

1. Field of the Invention

The invention relates to multispectral imaging systems that acquire images using at least two spectral bands simultaneously. The imaging systems 10 and 50 of the present invention are used, for example, for real-time detection of the contamination on agricultural commodities. The systems include an optical system comprising digital cameras, beam-splitters, lenses, and optical filters.

2. Description of the Related Art

To provide the means to ensure that the food supply is safe for consumers is the most critical mission for the food industry. Despite advances in food production and processing, there is still a need for technologies that can improve food safety. The USDA Economic Research Service estimated that microbial pathogens in food cause 6.5 to 33 million cases of human illness and up to 9,000 deaths in the U.S. each year, and cost approximately $5.6 to 9.6 billion annually in medical costs, hospitalizations, and lost work time (Busby et al., Bacterial foodborne disease: Medical costs and productivity losses. Agricultural Economics Report NO. (AER741). Washington D.C.: USDA Economic Research Service, 1996). Among these estimated costs, meat and poultry sources account for $4.5 to $7.5 billion. Potential contamination of meat and poultry sources can occur at the processing plant level when feces or ingesta are inadvertently deposited on the surface of the carcass. In order to prevent such contamination, the USDA Food Safety Inspection Service (FSIS) implemented a zero-tolerance policy that prohibits poultry carcasses from having any visible fecal contamination prior to entering the ice-water chiller tank (USDA, Enhanced poultry inspection, Proposed rule. Federal Register 59: 35659, Washington, D.C.; GPO 1994). This regulation, which is part of the FSIS Hazard Analysis Critical Control Point (HACCP) system, was designed to prevent bacterial cross-contamination among carcasses in the chiller tanks (USDA, Pathogen reduction, hazard analysis, and critical control point (HACCP) systems, final rule. Federal Register, 61:28805-38855. Washington, D.C.: GPO. 1996). With the implementation of HACCP, the food industry is mandated to establish science-based process controls, and to establish performance standards for these controls. Identification and separation of contaminated carcasses are critical to protecting the consumer from potential sources of food poisoning. At the same time, FSIS also modernized their inspection system (Busby, Food Review, Volume 20(1), 1997). However, the new program still relies on periodic human visual inspection to detect fecal contamination, which is labor intensive and prone to human error and variability. In addition, there has been a dramatic increase in water usage in most plants as a result of the zero-tolerance standard (Jones, Poultry, Volume 6, 38-41, 1999). Automated detection of fecal contaminants on raw meat, poultry, and other foodstuffs has been studied for a long time.

With poultry, for example, in a modern poultry processing plant, carcasses are placed on shackles of a processing line conveyor system for dressing and inspection. Typically, such conveyors operate at speeds of up to 140 carcasses per minute, with a six inch separation between shackles holding carcasses. Even with multiple inspectors continuously performing such inspection, as little as two seconds are allotted for the inspection of each carcass.

During this inspection period, the inspector is required to check for evidence of eight different diseases as well as for certain quality characteristics, to verify that the chicken was alive when placed on the production line, and to check for evidence of ingesta or fecal contamination. Moreover, during a typical business day operating in two eight hour shifts, a productive poultry processing plant may produce as many as 250,000 processed chickens.

After slaughter, each carcass is examined for disease or evidence of contamination that would render all or part of the carcass unfit for human consumption. Currently, the meat processing industry relies upon a variety of methods for the inspection of animal carcasses. These methods typically include human visual inspection, microbiological culture analysis, bioluminescent ATP-based assays, and antibody-based microbiological tests. Unfortunately, these procedures are labor intensive, time consuming, and do not meet the needs of the meat processing industry for an accurate high speed, non-invasive method that is amenable to inspection and real-time analysis.

A fluorescent technique can be used to detect feces from cow, deer, or swine by taking advantage of the presence of chlorophyll, which exhibits strong fluorescence emissions in the red regions of the spectrum, in the diets of those animals (Kim et al., Journal of Food Protection, Volume 66(7), 1198-1207, 2003).

Spectral sensing has been widely utilized for detecting foodborne contaminants. Techniques such as multispectral imaging, in which two to about ten different spectral bands image are obtained, and hyperspectral imaging, where up to several hundred contiguous spectral bands are measure, have been used for contaminant detection for poultry carcasses (Park et al., J. Food process Eng., Volume 27(5), 311-327, 2004; Heitschmidt et al., Trans. ASABE, Volume 50(4), 1427-1432, 2007). Researchers at the USDA Agricultural Research Service (ARS) have conducted spectroscopic analysis on poultry carcasses contaminated by feces and found that a ratio of the specific spectral bands (565 nm/517 nm) provides a good indication of the presence of fecal and ingesta contaminants on poultry carcasses (Windham et al., 2003).

Kim et al. (Journal of Food Engineering, Volume 71(1), 85-91, 2005) developed a transportable imaging system that detects fecal contamination of apples based on multispectral fluorescence image fusion. However, because the poultry diets do not contain as much chlorophylls as the diets of other animals, it is very difficult to utilize fluorescent techniques for poultry fecal detection.

Efforts have been made to develop automated or semiautomated visual inspection systems for detecting the presence of contaminants on food products during processing. Most systems utilize a technique in which the food item is irradiated with light having a frequency, for example, in the UV range, such that it causes the emission of fluorescent light radiation upon striking fecal matter or ingesta. Fluorescent light emanating from the target food item is then measured and compared with a threshold value. If the light gathered exceeds the threshold, a signal indicative of the presence of fecal contamination or ingesta is generated. Such a system is disclosed for example in U.S. Pat. Nos. 5,621,215 and 5,895,921 to Waldroup et al., and U.S. Pat. No. 5,821,546 to Xiao et al.

U.S. Pat. No. 5,914,247 to Casey et al. discloses a fecal and ingesta contamination detection system which is based on the premise that the emission of fluorescent light having a wavelength between about 660 and 680 nm is indicative of the presence of ingesta or fecal material. Thus, carcasses being processed are illuminated with UV or visible light (suitable wavelengths being between 300 and 600 nm) and the illuminated surface is then examined for the emission of fluorescent light in the 660 and 680 nm range. In a preferred embodiment, the intensity of such fluorescence in the 660-680 nm range is compared with that in the 600-620 nm range as a baseline in order to distinguish fluorescent light emissions of the carcasses themselves.

Visible and near-infrared reflectance (Vis/NIR) spectroscopy is a technique that can be used to detect contamination on foodstuffs. It is a nonconsumptive, instrumental method for fast, accurate, and precise evaluation of the chemical composition of agricultural materials (Williams, Commercial near-infrared reflectance analyzers. In Williams and Norris, eds., Near Infrared Technology in the Agricultural and Food Industries, Am. Assoc. Cereal Chem., St. Paul, Minn., 1987, pp. 107-142,). The use of Vis/NIR spectroscopic techniques for classifying wholesome, septicemic, and cadaver carcasses have been reported by Chen and Massie (ASAE, Volume 36(3), 863-889, 1993) and Chen et al., (Appl. Spectrosc., Volume 50, 910-916, 1996b). These studies were conducted with a near-infrared reflectance (NIR) probe in contact with a stationary carcass. Chen and Hruschka (ASAE Paper No. 983047, American Society of Agricultural Engineers, St. Joseph, Mich., 1999) disclosed an on-line transportable Vis/NIR system (400 to 1700 nm) in which the probe was not in contact with the carcass and carcasses were moving at rates of either 60 or 90 birds per minute. Carcasses were classified as wholesome or unwholesome with an average accuracy of 94% and 97.5% when measured in room light and in the dark, respectively. On-line trials were conducted in a slaughter establishment where spectra of normal and abnormal carcasses were measured. The Vis/NIR system measured carcasses at a rate of 70 birds per minute and was able to classify the carcasses from the spectral data with a success rate of 95% (Chen and Hruschka, 1998, supra). The Vis/NIR method showed promise for separation of wholesome and unwholesome carcasses in a partially automated system. The use of the technique to detect fecal and ingesta surface contaminants on poultry carcasses has not been attempted in the processing plant.

Machine vision is a technology for automating production processes with vision capabilities. Even though machine vision has evolved into a promising technology for many agricultural product applications, such as grading or inspection there are many factors to be considered in on-line applications; processing speed, reliability, and applicability for industrial environments (Sakar and Wolfe, Trans. ASAE, Volume 28(3), 970-979, 1985; Miller and Delwiche, Trans, ASAE, Volume 32(4), 1484-1490, 1989; Tao et al., Trans, ASAE, Volume 38(5), 1555-1561, 1995; Steinmez et al., Trans. ASAE, Volume 37(4), 1347-1353, 1994; Ni et al., ASAE Paper No. 933032, American Society of Agricultural Engineers, St. Joseph, Mich., 1993; Daley et al., Proc. SPIE, Volume 2345, 403-411, 1994). Image processing techniques have made machine vision research possible to identify and classify agricultural commodities in the spatial domain (Guyer et al., Trans. ADAE, Volume 29(6), 863-869, 1986) as well as in the spectral domain (Meyer et al., Applied Engineering in Agriculture, Volume 8(5), 715-722, 1992).

Machine vision techniques are feasible for grading and parts identification in poultry production (Daley et al., Proceedings of Robotics and Vision '88, Society of Manufacturing Engineers, Dearborn, Mich., 1988). Techniques for recognizing global or systemic defects on poultry carcasses with a color imaging system were reported by Daley et al. (1994, supra) and Chin et al., (Experimental evaluation of neural networks for inspection of chickens, Research Report of Georgia Tech. Research Institute, 1993). However, this approach had 90% accuracy for global defect classification and only 60% accuracy for local defect classification (Algorithms and techniques, RIA International Robots and Vision Conf., 1991). Even though a color imaging system has the ability to extract the salient image features, this system was not successful for totally automated inspection because of low accuracy (Daley, Color machine vision for industrial inspection advances and potential for the future, Research Report of Georgia Tech. Research Institute, 1992).

Multispectral imaging technology has potential for food inspection application. Since biological materials at different conditions have different spectral reflectance characteristics, the status of materials could be identified based on their spectral images by selecting optimum wavelengths. Several spectral image processing algorithms have been developed to differentiate wholesome carcasses from unwholesome carcasses (Park and Chen, ASAE Paper No. 946027, American Society of Agricultural Engineers, St. Joseph, Mich., 1994a; Park et al., Trans. ASAE, Volume 39(5), 1933-1941, 1996a). Use of intensities, recorded in different spectral bands of a multispectral camera for segmentation, was effective for classification of poultry carcasses (Park and Chen, Trans. ASAE, Volume 37(6), 1983-1988, 1994b; Park et al., 1996a, supra). Multispectral imaging was used for detecting unwholesome conditions, such as septicemia, cadaver, bruise, tumor, airsacculitis, and ascites, in poultry carcasses (Park et al., 1996a, supra). Park and Chen (1994b, supra) developed a prototype multispectral imaging system for detecting abnormal poultry carcasses, specifically to determine the optimal wavelengths of multispectral filters for discerning septicemic and cadaver carcasses from normal carcasses, and to develop a discriminate function for separation of the abnormal carcasses with an accuracy of 93% for normal, 83% for septicemic, and 97% for cadaver carcasses.

Textural feature analysis of multispectral images has potential to discriminate wholesome carcasses from septicemic and cadaver carcasses with high classification accuracy of about 94% (Park and Chen, Trans. ASAE, Volume 39(4), 1485-1491, 1996). However, texture feature analysis would not be useful for an on-line system because of heavy computing time. To achieve real-time processing and analyzing of multispectral gray-scale images for on-line separation of septicemic, cadaver, tumorous, bruised, and other damaged carcasses from the wholesome carcasses, a neural network algorithm was found to be useful (Park et al., ASAE Paper No. 983070, American Society of Agricultural Engineers, St. Joseph, Mich., 1998b). Thus, image texture analysis is an important process in scene analysis because it partitions an image into meaningful regions. Lumia et al., (Pattern Recognition, Volume 16(1), 39-46, 1983) described a method for discriminating texture classes based on the measurements of small regions determined by an initial segmentation of the image for categorizing homogeneous regions. Park and Chen (1996, supra) have reported that textural feature analysis of multispectral images containing Vis/NIR wavelengths based on co-occurrence matrices was feasible for discriminating abnormal from normal poultry carcasses at 542 nm.

Development of high speed and reliable inspection systems to ensure safe production of poultry processing has become an important issue. Two dual-wavelength vision systems were developed for on-line machine vision inspection of poultry carcasses (Chao et al., ASAE Paper No. 993118, American Society of Agricultural Engineers, St. Joseph, Mich., 1999). A real-time multispectral image processing algorithm was developed from neural network models with different learning rules and transfer functions for on-line poultry carcass inspection (Park et al., Journal of Agricultural Engineering Research, Volume 69, 351-363, 1998c). The classification accuracy with dual-wavelength spectral images was much higher than single wavelength spectral images in identifying unwholesome poultry carcasses (Chao et al., 1999, supra). Object oriented software was developed for on-line capture, off-line development of classification models, and on-line prediction of wholesome and unwholesome carcasses.

An extension of multispectral imaging is known as hyperspectral imaging which is also referred to as imaging spectrometry. Whereas multispectral imaging consists of measurements from two to about ten discrete wavelengths for a given image, hyperspectral imaging measures more than 10 contiguous wavelengths, often many more. Like multispectral imaging, hyperspectral imaging is an imaging technique that combines aspects of conventional imaging with spectrometry and radiometry. The result is a technique that is capable of providing an absolute radiometric measurement over a contiguous spectral range for each and every pixel of an image. Thus, data from a hyperspectral image contains two-dimensional spatial information plus spectral information over the spectral image. These data can be considered as a three dimensional hypercube which can provide physical and geometric observations of size dimension, orientation, shape, color, and texture, as well as chemical/molecular information such as water, fat, proteins, and other hydrogen-bonded constituent as described above in other Vis/NIR research. Hyperspectral imaging is often used in remote sensing applications (Schowengerdt, The nature of remote sensing, In: Remote Sensing: Models and Methods for Image Processing, San Diego, Academic Press, 1997, pp 1-33), but is also being utilized in medical, biological, agricultural, and industrial areas as well (Lu and Chen, SPIE, Volume 3544, 121-133, 1998; Heitschmdit et al., SPIE, Volume 3544, 134-137, 1998; Levenson et al., SPIE, Volume 3438, 300-312, 1998; Lu et al., ASAE Paper No. 993120, American Society of Agricultural Engineers, St. Joseph, Mich., 1999; Willoughby et al., SPIE, Volume 2599, 264-272, 1996).

While various systems have been developed for detecting contaminants on food, there still remains a need in the art for a more effective and portable system for detecting contaminants, especially fecal contaminants on poultry carcasses used for human consumption. The present invention, different from prior art systems, provides systems which are a portable multispectral imaging systems as well as a contaminant detection algorithm.

SUMMARY OF THE INVENTION

It is therefore an object of the present invention to provide portable multispectral imaging systems and methods for detecting contamination of foods.

Another object of the present invention is to provide portable imaging systems for detection of contamination on foods which achieves enhanced accuracy and dependability in positively identifying contaminants of foods.

A still further object of the present invention is to provide a portable multispectral imaging system for determination of contamination on food that has at least two cameras each having a charge-coupled device sensor capable of collecting at least two discrete narrow-band images, an illumination system in optical communication with said cameras, a front lens unit in optical communication with said at least two cameras, a beamsplitter in optical communication with said front lens and said at least two cameras, and at least two rear lens units in optical communication with said beamsplitter and said at least two cameras.

A still further object of the present invention is to provide a portable multispectral imaging system for determination of contamination on food that has at least two optical filters with one having a central wavelength of approximately 520 nm and the other having a central wavelength of approximately 560 nm.

A still further object of the present invention is to provide a portable multispectral imaging system for determination of contamination on food wherein said rear lens units each include two positive achromatic doublet lens each having a fixed aperture.

Another object of the present invention is to provide a portable multispectral imaging system for determination of contamination on food that has three cameras, each having a charge-coupled device sensor capable of collecting narrow-band images, an illumination system in optical communication with said cameras, a front lens in optical communication with said cameras, wherein said cameras each have a bandpass filters with two filters that are visible filters with central wavelengths of approximately 510 and 568 nm and the third is an IR/NIR bandpass filter.

A still further object of the present invention is to provide a portable multispectral imaging system for determination of contamination on food that has three cameras wherein said system has a cold mirror in optical communication between two of the three cameras through a beamsplitter located between the cold mirror and one of the cameras.

Another object of the present invention is to provide a portable multispectral imaging system for determination of contamination on food that has at least two cameras each having a charge-coupled device sensor capable of collecting at least two discrete narrow-band images and an illumination system wherein said illumination system includes ring-type light emitting diode lights encircling a front lens and further including a heat sink.

Further objects and advantages of the invention will become apparent from the following description.

BRIEF DESCRIPTION OF THE DRAWINGS

FIG. 4a is an image taken by port 1 and FIG. 4b is an overlay image of port 1 with the image taken by port 2.

FIG. 6a shows an overlay image of port 1 with the image of port 2 at the region of interest, and FIG. 6b shows the spatial distribution of the calibration error, where dot diameter indicates the size of error.

FIG. 7a shows four types of contaminants that were manually deposited on the carcass surface. From the top: duodenum, cecum, colon, and ingesta) FIG. 7(b) shows the result of the contaminant detection with threshold T=1.02; and FIG. 7(c) shows the result of the contaminant detection with threshold T=1.10.

FIG. 11a shows composite image of grid distortion target; and FIG. 11b shows three-band image of a 3-D object.

DETAILED DESCRIPTION OF THE INVENTION

Figure 1:
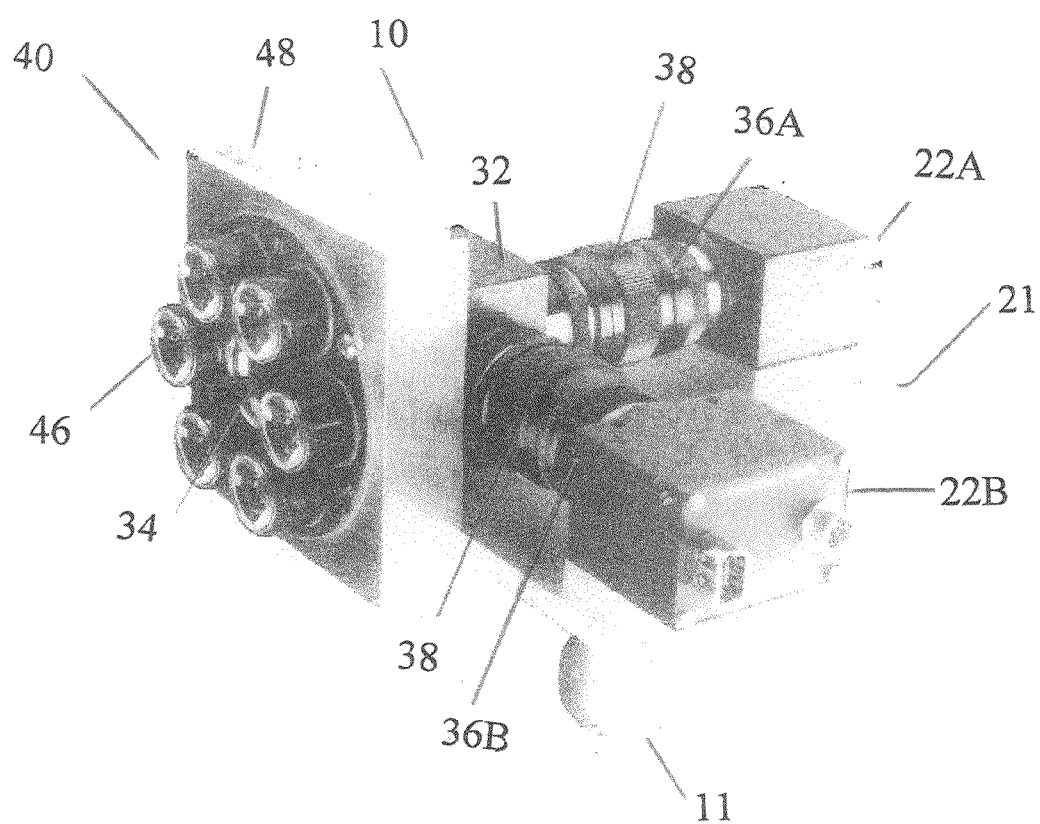
FIG. 1 is an illustration of handheld multispectral imaging system 10 showing a two port system having two cameras 22a and 22b, bandpass filters 36, front lens unit 34, rear lens units 38, beamsplitter 32, illumination system 40, LEDs 46 and grip 11.
Figure 9:
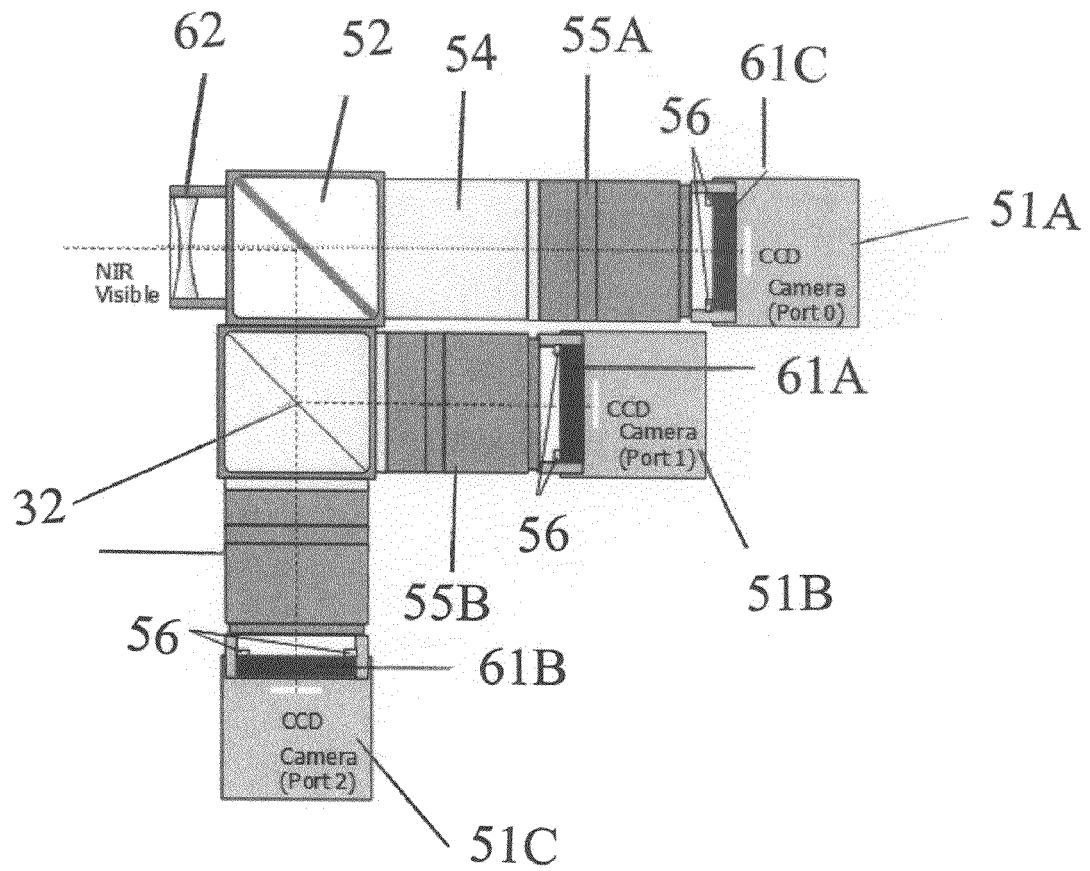
FIG. 9 is an optical diagram of the three-band spectral imaging system 50 showing front lens unit 62, cold mirror 52, spacer 54, 35 mm lens A, B, and C; C-mount ring retainers A, B, and C; NIR Bandpass filter 61c, CCD cameras designated as port 0, port 1, and port 2 55a, 55b, and 55c; CCD sensors 27, beamsplitter 32, and visible bandpass filters 61a and 61b.
Figure 10:
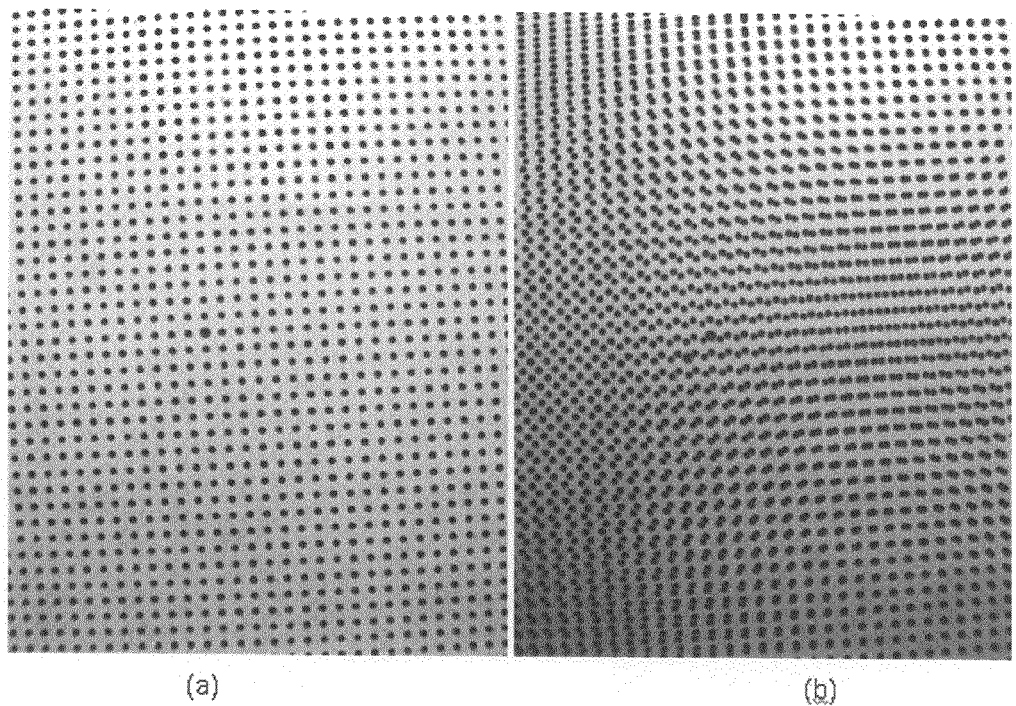
FIGS. 10a and 10b show images of grid distortion target taken by the three-band spectral imaging system; (a) shows the image of port 1; and (b) overlay image of port 1 with the image of port 2.

The present invention is to multi-band spectral imaging systems 10 and 50 for detecting fecal contaminants on poultry carcasses based on a band-ratio algorithm (FIGS. 1 and 9). Imaging system 10 acquires two-band images at any wavelength in the approximately 400 to 1000 nm portion of the spectrum simultaneously by utilizing two interchangeable optical filters 36, two monochrome cameras 22, and various optical components as described below. Systems 10 and 50 of the present invention includes an optical system 20 that includes a two-port camera system 21 (FIGS. 1 and 2) or a three-port camera system 51 (FIG. 9). System 21 includes two cameras 22 (EC1380, Procilica, British Columbia, Canada), an optical system 30 that includes a beamsplitter 32 (Edmund Optics, Barrington, N.J.) front lens units 34 (Edmund Optics), rear lens units 38 (Edmund Optics), and two narrow bandpass filters 36 (Omega Optical Inc, Brattleboro, Vt.) as shown in FIG. 1. Systems 10 and 50 further include an illumination system 40, a camera trigger unit 24, and a portable computer 26 (FIGS. 1-3 for system 10; not shown for system 50).

Figure 2:
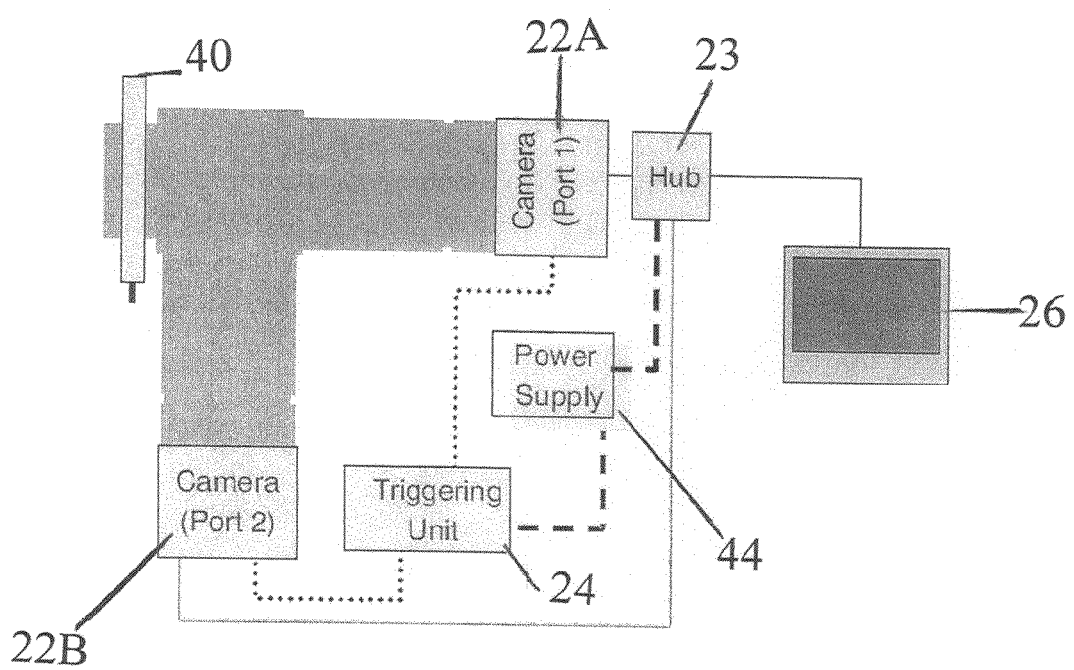
FIG. 2 is a schematic drawing of dual port imaging system 10 showing CCD camera port 1 22a and port 2 22b, hub 23, triggering unit 24, and illumination system 40.

FIG. 2 shows a schematic diagram of imaging system 10. A Windows XP-based handheld computer 26 (OQO model 01+, San Francisco, Calif.) is used for image acquisition, processing and displaying. Any handheld computer 26 that can perform image acquisition, processing and displaying is useful in the present invention, which is within the ordinary skill in the art. The system calibration and contaminant detection algorithms, described below, were developed with C++ programming (Microsoft Visual Studio.net, Microsoft, Seattle, Wash.) and loaded on handheld PC 26. PC 26 is connected to a hub port 23 by IEEE 1394A FireWire cable 45 to communicate with cameras 22a and 22b. Because PC 26 does not have a function to provide power to the cameras, a 12 VDC power supply 44 supplied power to hub 23 which delivers power to cameras 22a and 22b via a FireWire cable 45. Cameras 22a and 22b are operated in external trigger mode to synchronize image acquisition timing. External Trigger generator 24 is based on a microcontroller (PIC16F877, Microchip, Chandler, Ariz.) and generates two identical TTL (Transistor-Transistor Logic) signals for triggering the cameras. The trigger generator can be operated in two modes, a sensor mode and a continuous mode. In the sensor mode, the trigger generator is connected with a photoelectric sensor (PZ-V31, Keyence, Osaka, Japan) that detects movement of the shackle carrying chicken carcasses so that the imaging system is allowed to capture the image when the carcass crosses the front of the imaging system. The continuous mode triggers the imaging system continuously from a stationary object. Cameras 22a and 22b are equibed with an approximately 10.2×8.3 mm (⅔ inch) Charged Coupled Device (CCD) 27 that collects high-resolution (1360×1024 pixels) imagery at up to about 10 frames per second. Each camera 22a and 22b is capable of acquiring either 8-bit or 12-bit monochrome images. For the present invention, 12-bit monochrome images are simultaneously acquired from both cameras 22a and 22b at a rage of approximately 5 frames per second. Each image is binned using the camera's 2×2 binning mode. Binning is a method of summing the signal in adjacent pixels at the cost of image resolution. Because the bandpass filters use in the imaging system are very narrow, the intensity of light received by the imaging sensor is very low. With 2×2 binning, the resulting image possesses about a four fold increase in sensor level versus the original image, although with just half the spatial resolution of the original image sizes (approximately 680× 512 pixels).

The specifications for the two port imaging system 10 are summarized in Table 1 below.

TABLE 1

| Specifications for Two Port Imaging System 10 | |
|---|---|
| Weight | Approx. 1160 grams (approx. 652 grams for cameras and lenses |
| Size | Approx. 150 mm (w) × 150 mm (L) × 50 mm (H) without LED light and grip |
| Illuminator | Ring type with six LEDs and a heat sink |
| | Diameter of the ring: Approx. 74.5 mm |
| | Typical lunious flux: approx. 125 lm |
| | Color Temperature: approx. 5500 K |
| | Typical Power Consumption: Approx. 7 W |
| Camera | Prosilica EC1380 |
| | Sensor: Approx. ⅔ inch CCD (ICX285AL, Sony Corp., Tokyo, Japan) |
| | Resolution: Approx. 1360 × 1024 |
| | Digitization: 8 or 12 bits |
| | C mount |
| Console Device | OQO Model 01+ |
| | Size: Approx. 125 mm (W) × 90 (L) × 25 mm (H) |
| | Processor: TM5800 999 MHz, 488 M of RAM |
| | OS: Windows XP Professional |
| | Estimated Life with a battery: Approx: 2.5 hours |
| Optical Filter for Port 1 | Interference Bandpass filter, CWL 520 nm, FWHM 10 nm, transmittance ≧65% |
| Optical Filter for Port 2 | Interference Bandpass filter, CWL 560 nm, FWHM 10 nm, transmittance ≧65% |

Figure 3:
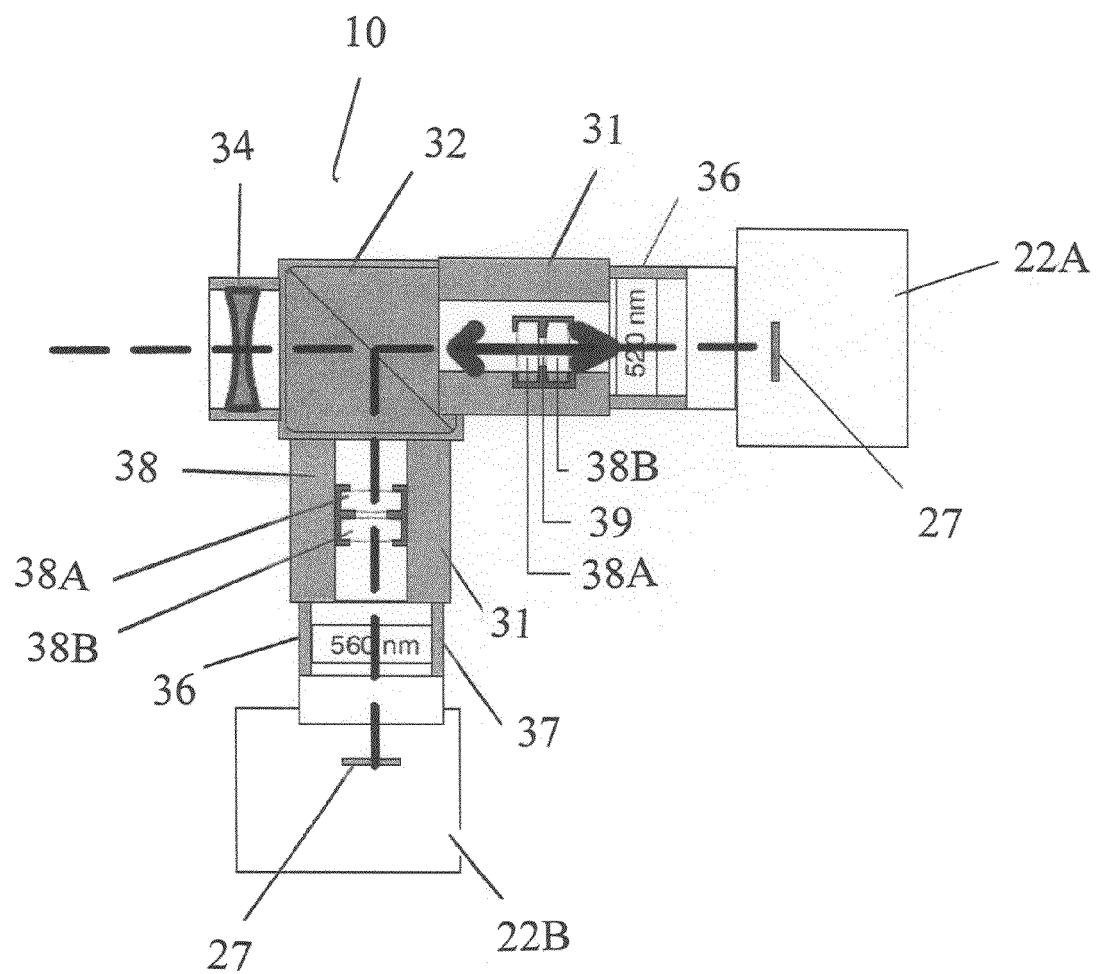
FIG. 3 is a drawing showing the optical design of the two port multispectral imaging system 10 showing camera port 1 22a, camera port 2 22b, CCD sensors 27, Rear lens 38a, Rear lens 38b, bandpass filters 36, beamsplitter 32, and front lens unit 34.

Optical System 30 is shown in FIG. 3 and includes front lens units 34, rear lens units 38, beamsplitter 32, and two bandpass filters 36. The two interference bandpass filters 36 have central wavelengths (CWL) at approximately 520 nm 36a and approximately 560 nm 36b with approximately 10 nm full width half maximum (FWHM), respectively (Omega Optical, Inc.) were installed for poultry inspection. Narrow bandpass filters 36 are enclosed in the C-mount barrels 37 which are attached in front of respective cameras.

Because systems 10 and 50 are handheld, i.e. portable, and are used at short working distance, systems 10 and 50 have to cover a wider field-of-use. The desired focal length of lens units 34 and 38 have to be much shorter than the physical length. Such a lens configuration can be found in a wide-angle lens design which has strong negatively powered elements in front of the main body of the lens to cover wider field angels by bending the rays outward. The lens configuration design for the two port imaging system 10 has a negative-powered element in front lens unit 34 or 55. In system 10 a negative achromatic doublet 34a and 34b, is used as front lens unit 34. The collimated light by front lens unit 34 is split into two ways by cube-beamsplitter 32 that reflects approximately 50% of the light at approximately a 90 degree angle and it is transmits the other approximately 50% straight through. System 50 is described below.

Rear lens unit 38 consists of two positive achromatic doublet lenses 38a and 38b and a fixed aperture. System 10 contains two identical rear lenses units 38; each unit focuses an image on its respective CCD sensor 27 of cameras 22a and 22b. (FIGS. 1-3). Rear lens units 38 are capsulated by a helicord barrel 31 that allows the lenses 38a and 38b to travel up to approximately 7.5 mm along the optical axis (See FIG. 3). Proper focus for each camera 22 can be attained independently and instantly by adjusting the helicoid 31. A fixed aperture 39 (approximately 4 mm diameter) is placed between the two achromatic doublets 38 (FIG. 3) this small aperture 39 helps to reduce off-axis aberrations that cause severe blur due to the large field-of-view by limiting the bundle of rays going through optical system 30. The addition of aperture 39 produces an image with a reduced level of brightness.

Narrow bandpass filter 36, enclosed in a C-mount barrel 37, is attached at each end of rear lens unit 38. The advantages include easy access to filters 36, which are interchangeable without a complicated manufacturing process, the filters are not integrated with the cameras 22a and 22b (Duncan and Kantor, 1996), and the user has the flexibility to change spectral bands based on the given imaging needs. Furthermore, filters 36 are placed directly behind the front lens unit 34. This is important because interference filters are extremely sensitive to the angle of the input and hence are intended only for collimated input. These off-the-shelf filters are as close to the about 517 nm and about 565 nm as possible (Park et al. 2004).

The paraxial specifications of imaging system 10 are shown in Table 2.

TABLE 2

Optical System paraxial specifications.

| | |
|---|---|
| Front Lens | −50 mm negative achromatic doublet, 25 mm diameter |
| Rear Lens A | 75 mm achromatic doublet, 12.5 diameter |
| Rear Lens B | 40 mm achromatic doublet, 12.5 mm diameter |
| Beamsplitter | Material: BK7, transmit and reflect: 50% ± 5% at 550 mm9 cube size: 35 mm |
| Number of lens elements | 5 |
| System Focal Length | 13.7 mm |
| Working F# | 7.7 |
| Stop Radius | 2.0 mm |
| Physical Distance from front lens to CCD | 106 mm |

A ring-type light emitting diode (LED) light 46 (Lumileds, San Jose, Calif.) consisting of 6 white LEDs 46 (5500 Kelvin) and a heat sink 48 attached around the perimeter of system 10's front lens unit 34. LED illumination is very suitable for a handheld imaging system because of its low energy consumption, low heat generation, and compactness. With six LEDs 46, Illumination system 40 produces about 125 Im at about 700 mA. Typical power consumption is approximately 7 W. Each LED 46 is covered by a plastic lens 34 that controls light distribution. Illumination system 40 can be easily detached from imaging systems 10 and 50.

Figure 4A:
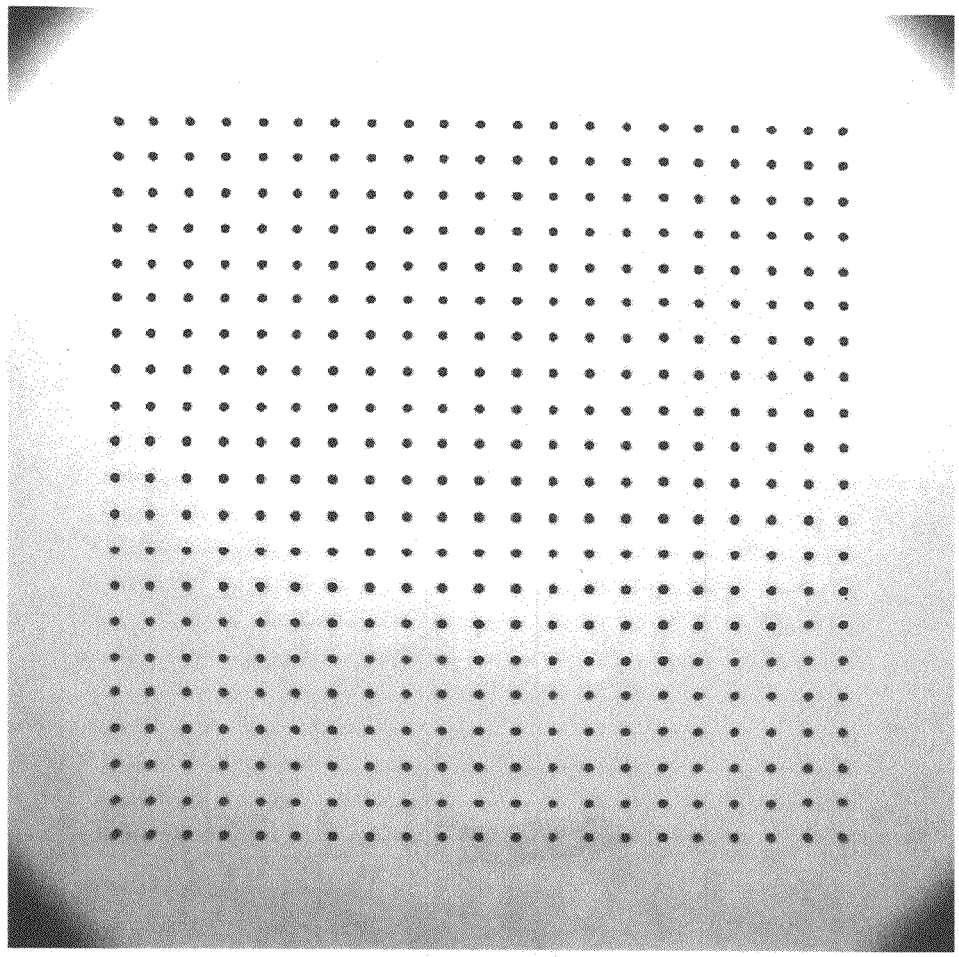
FIGS. 4a-4b are photographs of images of grid distortion target taken by the two port imaging system 10.
Figure 4B:
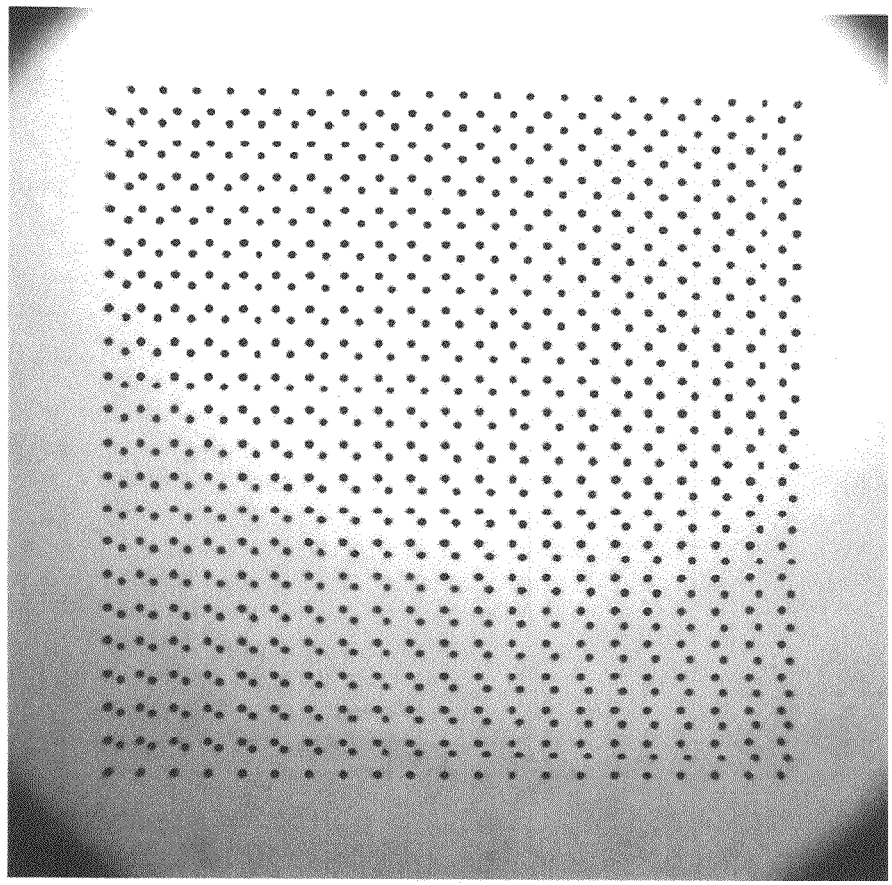

Initial imagery taken by the two-band spectral imaging system 10 suffered from image-to-image misalignment, as shown in FIG. 4. The images show a fixed frequency grid distortion target that has a total of 441 (21×21) dots, each approximately 2 mm in diameter with an approximately 10 mm spacing taken by imaging system 10 at about a 60 cm working distance. FIG. 4a shows the image taken by the port 1 camera 22a. FIG. 4b is a composition of two images in which all dots in the image of port 1 (FIG. 4a) are projected onto an image collected through port 2. It should be noted that in this case a high-power illumination source was used instead of LED light for the purpose of maximizing image quality. Illumination system 40 used for the acquisition of FIGS. 4a and 4b was a 500 W, 3200 kelvin incandescent lamp (Starlite QL, Photflex, Watsonville, Cal) which was fitted by a soft box (SilverDome NXT, Photoflex) that diffused the light source. An alignment error between the two cameras can be seen. Overall lens quality and a lack of precision inherent in the camera manufacturing process contributed to the geometric misalignment between the two image coordinates. The total position tolerance of the cameras 22a and 22b is about ±0.25 mm. Considering the size of the pixel of the sensor (approximately 12.9 μm for 2×2 binning), the sensor positioning tolerance could cause about a ±39 pixels error. The lens units 38 also contribute to the coordinate misalignment. Even though the two rear lens units 38a and 38b have an identical design, the images formed by the two units 38a and 38b are slightly different because of lens manufacturing tolerances.

Such lens manufacturing tolerances also have to be taken into account (Fischer and Tadic-Galeb, 2000).

Camera calibration includes two steps (Kise et al., 2007): First, correcting a lens-oriented error by applying a mathematical lens distortion model; and second, correcting a sensor positioning error based on 2D linear projection. A lens distortion of the image is corrected by applying a mathematical lens distortion model to the distorted image. It is known that the most dominant factor contribution to lens distortion is the radial component, with emphasis on the first term (Weng et al., 1992). The mathematical model of radial distortion is expressed by equation 1:

$$\delta r = a_1 \rho^3 + a_2 \rho^5 + a_3 \rho^7 + L \quad (1)$$

where $\rho$ is the radial distance from the lens center, and $a_1$, $a_2$, $a_3$, . . . , are the coefficients of radial distortion. A second-order radial distortion model is used in the present invention for the lens distortion correction (Zhang, 1998).

As a result of the lens distortion correction, the unique distortions were eliminated from the original images. That is, the new undistorted image coordinates could be modeled by the pinhole camera geometry. Given that the two image coordinates can be modeled by the pinhole geometry and the optical axes of two coordinates are aligned by the described combination of linear transformations, such as a rotation, translation, and dilation (Faugeras, 1993). Let a given point $m_1=(x_1,y_1)^T$ in the port 1 image and $m_2=(x_2,y_2)^T$ in port 2 image represent the same point in the world coordinates. The geometric relationship of these two points can be described by equation 2:

$$\begin{pmatrix} x_1 \\ y_1 \end{pmatrix} = H \begin{pmatrix} x_2 \\ y_2 \\ 1 \end{pmatrix} \qquad (2)$$

where H is the 2×3 projection matrix. With some known corresponding points between two images, a unique projection matrix H can be calculated by a least squares method. The image of the distortion target shown in FIG. 4 was used to calculate the projection matrix H.

Figure 5:
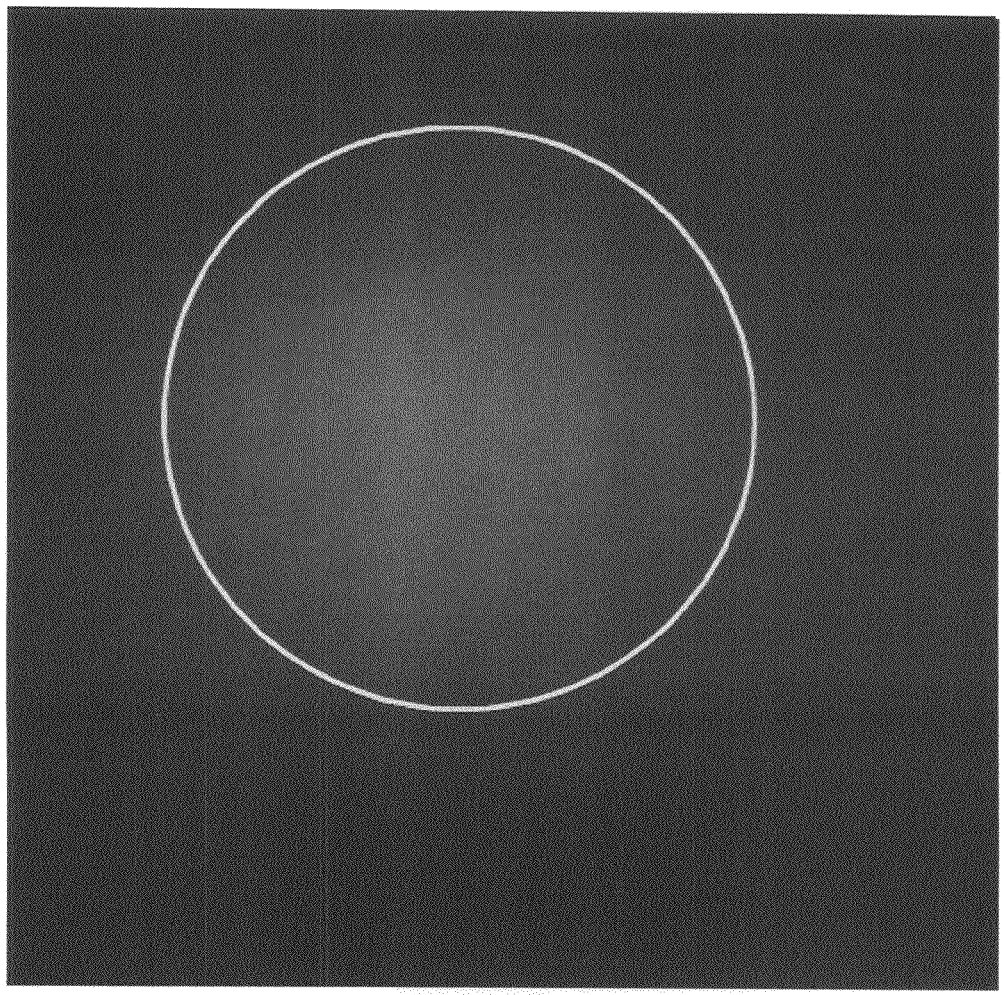
FIG. 5 is an image of a 99% reflectance panel illuminated by the LED 46. The white circle suggests the determined ROI of the image.
Figure 12:
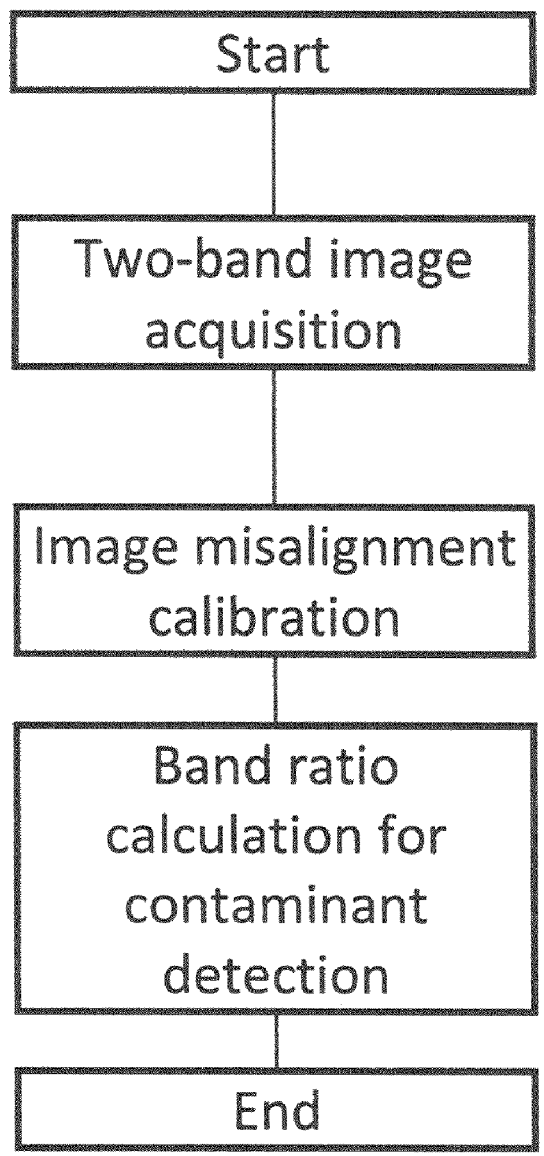
FIG. 12 is a flow chart for two port imaging system 10.

FIG. 5 is an image of an about 99% reflectance panel (Labsphere, North Sutton, Ohio) taken by imaging system 10, outfitted with the LED ring light at 60 cm distance. The exposure time of both cameras 22a and 22b was approximately 30 ms. Camera 22a and 22b gain settings were approximately 11 dB and 7 dB for port 1 (520 nm) and port 2 (560 nm), respectively, to compensate for the spectral difference of the LED at the respective wavelengths. It was apparent that the LED light could not illuminate the entire field of view. Thus, the region of interest (ROI) of the image was limited to the region that the LED could illuminate sufficiently. The center to the ROI ($C_x, C_y$) was calculated by a following reflectance-weighted average function:

$$C_x = \frac{1}{S} \sum_{x=0}^{Nx-1} \sum_{y=0}^{Ny-1} r(x,y) \cdot x \qquad (3)$$

$$C_y = \frac{1}{S} \sum_{x=0}^{Nx-1} \sum_{y=0}^{Ny} r(x,y) \cdot x \qquad (4)$$

$$S = \sum_{x=0}^{Nx-1} \sum_{y=0}^{Ny-1} r(x,y) \qquad (5)$$

where S represents the sum of all reflectance values of the image; $N_x$ and $N_y$ are the resolution of the image in the x and y axes, respectively, and r(x,y) is the reflectance value of the image at (x,y). By applying these equations to the image in FIG. 5, the center of the ROI was identified (approximately 328.9, 265.8). The radius of the ROI was determined to be approximately 150 pixels. As a result, the reflectance within the ROI ranged approximately from 25% to approximately 45% (FIG. 12).

Figure 8:
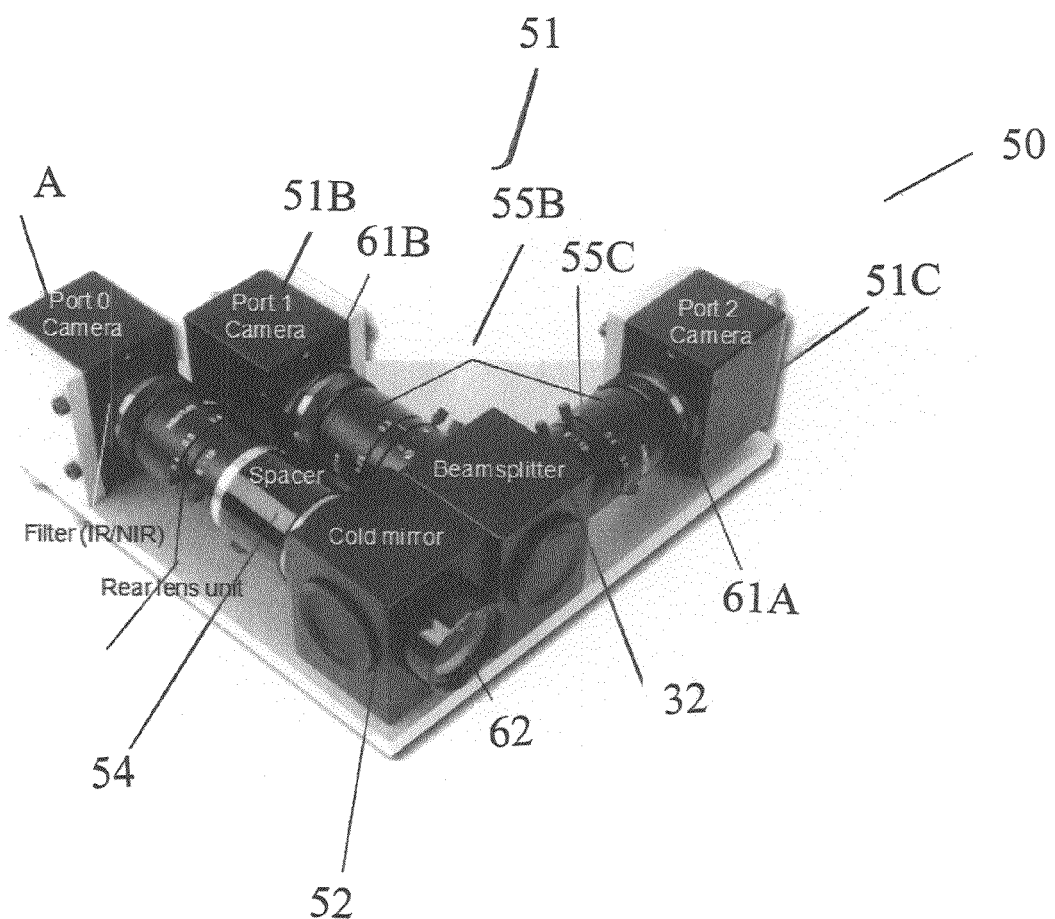
FIG. 8 is a photograph showing a three-band spectral imaging system comprising a three-port camera system 50 having three identical monochrome cameras 51a, 51b, 51c; cold mirror 52, beamsplitter 32, lens units 62 and 55 and three optical filters 61a, 61b, and 61c.

Three-port imaging system 50 (FIGS. 8 and 9) acquires three-band images at any wavelength in the approximately 400 to 100 nm portion of the spectrum simultaneously by utilized three interchangeable optical filters that are bandpass filters 36 including two visible bandpass filters 36a and 36b; and a IR/NIR bandpass filter 36c as shown in FIG. 9, three monochrome cameras 51a, 51b, and 51c; and various optical components as described below. System 50 of the present invention includes an optical system 20 that includes a three-port camera system 51. System 51 includes three cameras 51a, 51b, and 51c (EC1380, Prosilica, British Columbia, Canada) equipped with a ⅔ inch CCD sensor 27 that acquires high-resolution (approximately 1360×1024 pixels), 12-bit monochrome images at up to about 10 frames per second. Spatial binning is set at 2×2 for all images acquired. These settings result in images of approximately 680 pixel×512 pixel. Cameras 51a, 51b, and 51c accept C-mount components and have an IEEE1394A Firewire port (not shown). Optical system 60 for system 50 includes one beamsplitter 32 (Edmonds optics, Barrington, N.J.), and three, front lens units 62, (Edmond Optics), three rear 35 mm lens units 51 (Edmond Optics), three bandpass filters 61a, 61b and 61c where 61a and 61b are visible filters and 61c is a IR/NIR filter (Omega Optical, Inc.); and cold mirror 52 (Edmond Optics) as shown in FIGS. 8 and 9. System 10 further includes a spacer 54 located between Port 0 camera 51a rear lens unit 38 and cold mirror 52, a camera trigger unit (not shown) and a portable computer as described above (not shown).

FIG. 9 shows an optical diagram of the three-band spectral imaging system 50. The optical components of system 50 include a front lens unit 62, a cold mirror 52, a beamsplitter 32, three bandpass filters 61a, 62b, and 62c, and three rear lens units 51. Front lens unit 62 is a −30 mm negative achromatic lens with a 25 mm diameter (Edmunds Optics). An incident light is collimated by front lens 62, and then spilt into two paths by cold mirror 52 (Edmunds Optics) which reflects approximately 90% visible light and transmits approximately 80% infrared/near infrared (IR/NIR) straight through to Port 0 camera 51a. The visible light is further split identically by cube-beamsplitter 32 (Edmund Optics) which reflects approximately 50% of the light at a right angle and transmits the other approximately 50% straight through to Port 1 camera 51b. To compensate for the optical path differences, a spacer 54 that has the same optical length of beamsplitter 32 is attached behind cold mirror 52.

Identical rear lens unit 38 focuses images on the CCD sensor 27 of each camera 51a, 51b, and 51c. Rear lens units 55a, 55b, and 55c include a C-mount lens (35HB, Tamuron, Saitama, Japan). The lens has a 35 mm fixed focal length and its focus and iris can be adjusted manually which allows the images to be independently focused on each cameras' 22 CCD sensor 27.

An optical filter is fixed within the mount of each camera 51a, 51b, and 51c by a C-mount ring retainer 56. This design grants easy access to the filters, thus enabling the system to be retrofitted for a variety of applications such as remote sensing (Yang et al., 2003), food safety and quality inspection (Heitschmidt et al., 2007; Kawamura et al., 2007) fruit mutuality detecting (Noh et al., 2007), and mineral inclusion analysis (Williams et, 1993). This is a great advantage in terms of flexibility of the spectral bands selection, s compared to other multispectral imaging systems that integrate filters and sensors as a complete module. Three narrow bandpass interference filters 61a, 61b, and 61c with approximately a 24.1 mm diameter (Edmunds Optics) are implemented for poultry contaminant detection (Park et al., 2006). Two visible filters 61a and 61b have central wavelengths (CWL) at approximately 510 nm and 568 nm with an approximately 10 nm Full-Width, Half-Maximum (FWHM), respectively. The NIR filter 61c has an approximately 800 nm CWL and approximately a 40 nm FWHM. The paraxial specifications of the three port imaging system 50 are summarized below in Table 3.

TABLE 3

Optical System paraxial specifications.

| | |
|---|---|
| Front Lens | −30 nm negative achromatic doublet, 25 mm diameter |
| Rear Lens | 35 mm Fixed focal lens, Manual focus, Manual iris, F-stop: 2.1-22 |
| Cold Mirror | Substrate: BOROFLOAT ™, Thickness: 3.3 mm, Reflectance: 90% visible light, Transmission: 80% IR waves |
| Beamsplitter | Material: BK7, transmit and reflect: 50% ± 5% at 550 nm, cube size: 35 mm |
| System Focal Length | 12.8 mm |
| Physical distance from fronts lens to CCD | 140 mm |
| Optical filter for Port 0 | Intereference bandpass filter, CWL 800 nm, FWHM 10 nm, 24.15 Dia., transmittance ≧50% |
| Optical Filter for Port 1 | Interference bandpass filter, CWL 510 nm, FWHM 10 nm, 24.15 mm dia., transmittance ≧45% |
| Optical filter for port 2 | Interference bandpass filter, CWL 568 nm, FWHM 40 nm, 24.15 mm dia., transmittance ≧45% |

Figure 13:
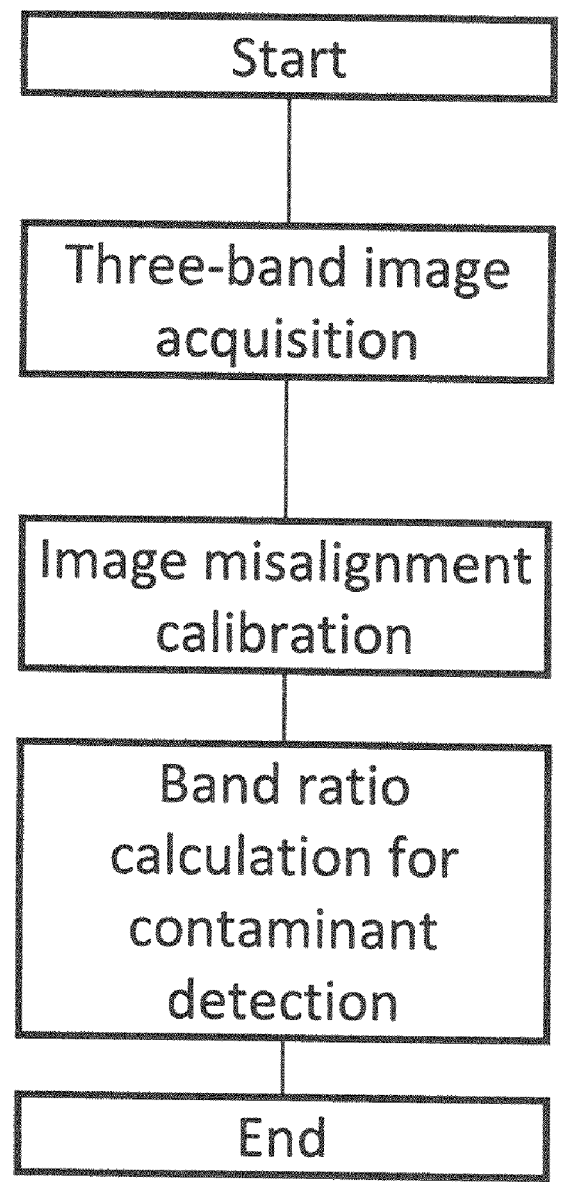
FIG. 13 is a flow chart for three port imaging system 50.

As the two port camera system 10 exhibits image misalignment shown in FIG. 4, raw imagery taken by three port camera system 50 also suffers from image misalignment. The same image calibration method described for two port system 10 (Equations (1) and (2) is used for the image misalignment correcting for the three port camera system 50 (FIG. 13).

The following examples are intended only to further illustrate then invention and are not intended to limit the scope of the invention which is defined by the claims are used as a model for the system of the present invention.

EXAMPLE 1

A series of two-band images were collected to evaluate system 10 calibration accuracy. With System 10 fixed on an optical table (Model 784-439, TMC, Peabody, Mass.), the distortion target was placed perpendicular to the optical axis of imaging system 10 at five different distances: approximately 50, 55, 60, 65, and 70 cm. The same illumination system used for acquiring the image shown in FIG. 4 was used for the image collection. Two-band images were taken at each distance and subsequently calibrated as described above in the detailed description of the invention. The centroids of each dot were determined by a customized image processing method: simple thresholding identified the pixels that represented each dot. The dot's centroids were calculated by averaging their pixel locations. The image misalignment error was determined by calculating the offset distance of corresponding centroids between the two-band images.

Figure 6A:
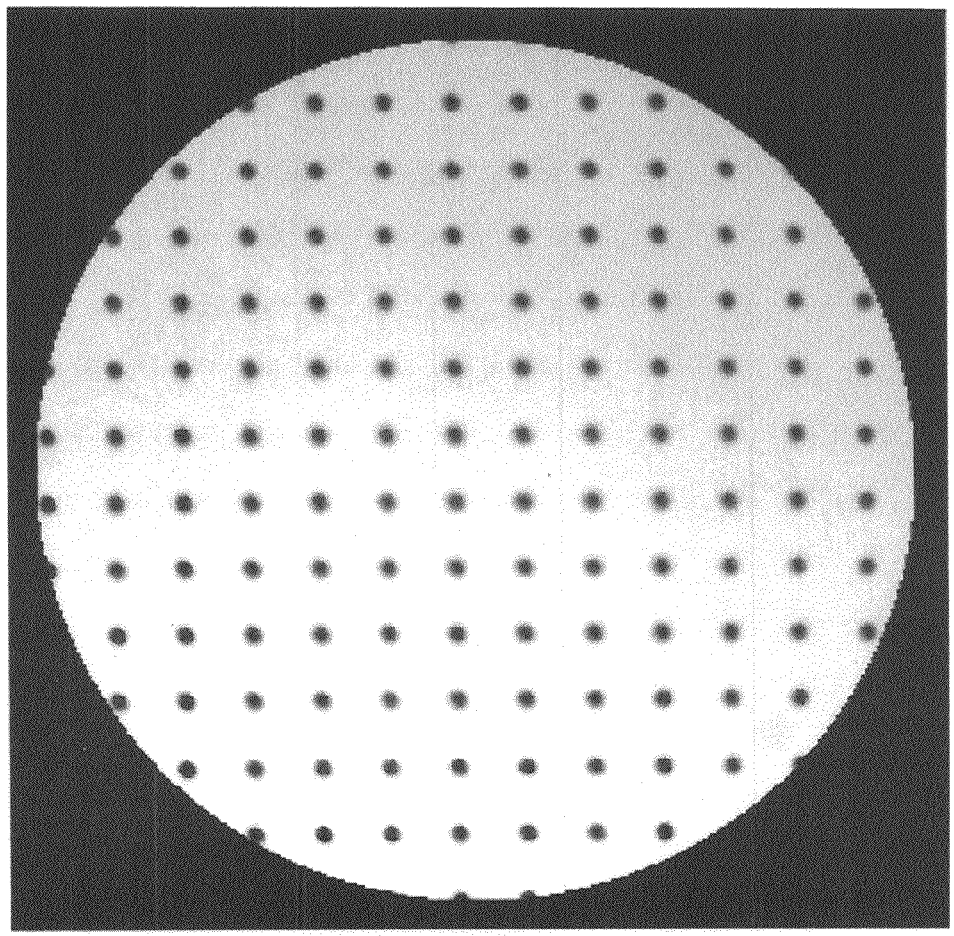
FIGS. 6a and 6b are images that are a result of system calibration at approximately 50 cm distance.
Figure 6B:
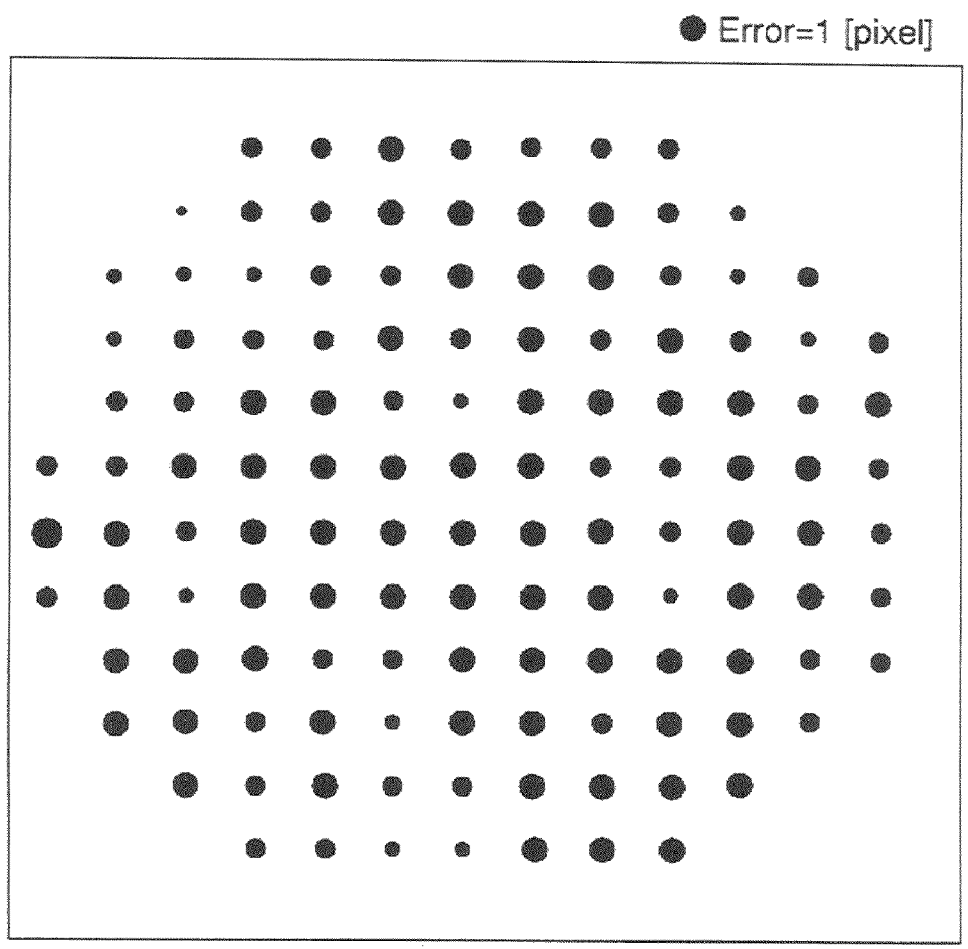

As a result of system 10 calibration, two-band images are registered accurately, as shown in FIGS. 6a and 6b. A composite image collected at approximately 50 cm working distance (FIG. 6a) shows that the misalignment of the two images, apparent in FIG. 4, was corrected; all dots in the ROI were accurately aligned over two images. The bubble chart (FIG. 6b) shows a spatial distribution of the misalignment error over the image. The size of the bubble at each location indicates the offset distance between the corresponding dots in the composite image. Accordingly, the calibration accuracy was shown to be fairly uniform over the image, with only 12 of the 129 dots possessing an error larger than one pixel. One pixel error was equivalent to approximately 12.9 µm of CCD sensor 27 positioning error. The average error over the image was approximately 0.76 pixels or approximately 9.8 µm, which resulted in approximately 2 mm registration error at a calibration target distance of approximately 50 cm.

The test results at all distances (approximately 50, 55, 60, 65, and 70 cm) are summarized below in Table 3. Overall, very similar results were obtained at all distances, except at approximately 60 cm. The reason why an exceptionally good result was obtained at approximately 60 cm was that the system calibration parameters were identified based on images taken around 60 cm. For the purpose of comparison, misalignment errors without calibration are listed as well. Without the calibration, the average image misalignment error for all distances was approximately 20.75 pixels or approximately 267.7 µm. This error was within the given sensor positioning tolerance (±250 µm).

Because the target object is a chicken carcass, it was very important to show that the system calibration was valid on 3-D objects. In order to function as a handheld system, it is also important for imaging system to work at various working distances because the distance between imaging system 10 and the target is expected to vary significantly. The results show that the two-band system 10, along with the system calibration could provide registered imagery of 3-D objects consistently with less than one-pixel error, regardless of working distance.

TABLE 4

Result of system calibration at five distances.

| | Calibrated System | | | | Uncalibrated System | | | |
|---|---|---|---|---|---|---|---|---|
| | Average Error | | Max. Error | | Average Error | | Max. Error | |
| Distance (cm) | µm | pixel | µm | pixel | µm | pixel | µm | pixel |
| 50 | 9.8 | 0.76 | 14.6 | 1.13 | 267.7 | 20.75 | 304.1 | 23.57 |
| 55 | 9.5 | 0.74 | 17.0 | 1.32 | 268.2 | 20.79 | 303.4 | 23.52 |
| 60 | 5.7 | 0.44 | 11.5 | 0.89 | 266.0 | 20.62 | 303.2 | 23.50 |
| 65 | 9.2 | 0.71 | 15.4 | 1.19 | 268.3 | 20.80 | 305.7 | 23.70 |
| 70 | 8.9 | 0.69 | 16.3 | 1.26 | 268.2 | 20.79 | 302.6 | 23.46 |
| Average | 8.6 | 0.62 | 20.4 | 1.57 | 267.7 | 20.75 | 305.7 | 23.70 |
| SD | 1.7 | 0.13 | 2.1 | 0.17 | 1.0 | 0.08 | 1.2 | 0.09 |

EXAMPLE 2

The imaging system and the image correction algorithm were tested with chicken carcass contaminated with chicken feces (duodenum, cecum, colon) and ingesta. Sample chicken carcasses were obtained from a local poultry processing factory after an evisceration and washing process. In addition, unprocessed carcasses were also obtained and these unprocessed carcasses were manually eviscerated to collect fecal samples. Each carcass was hung on a stationary shackle upside down facing imaging system 10 at a object distance of approximately 60 cm nominal working distance. Fecal and ingesta samples were manually applied to the carcass surface at several locations. Two-band images were acquired by imaging system 10 using LED light.

Figure 7:
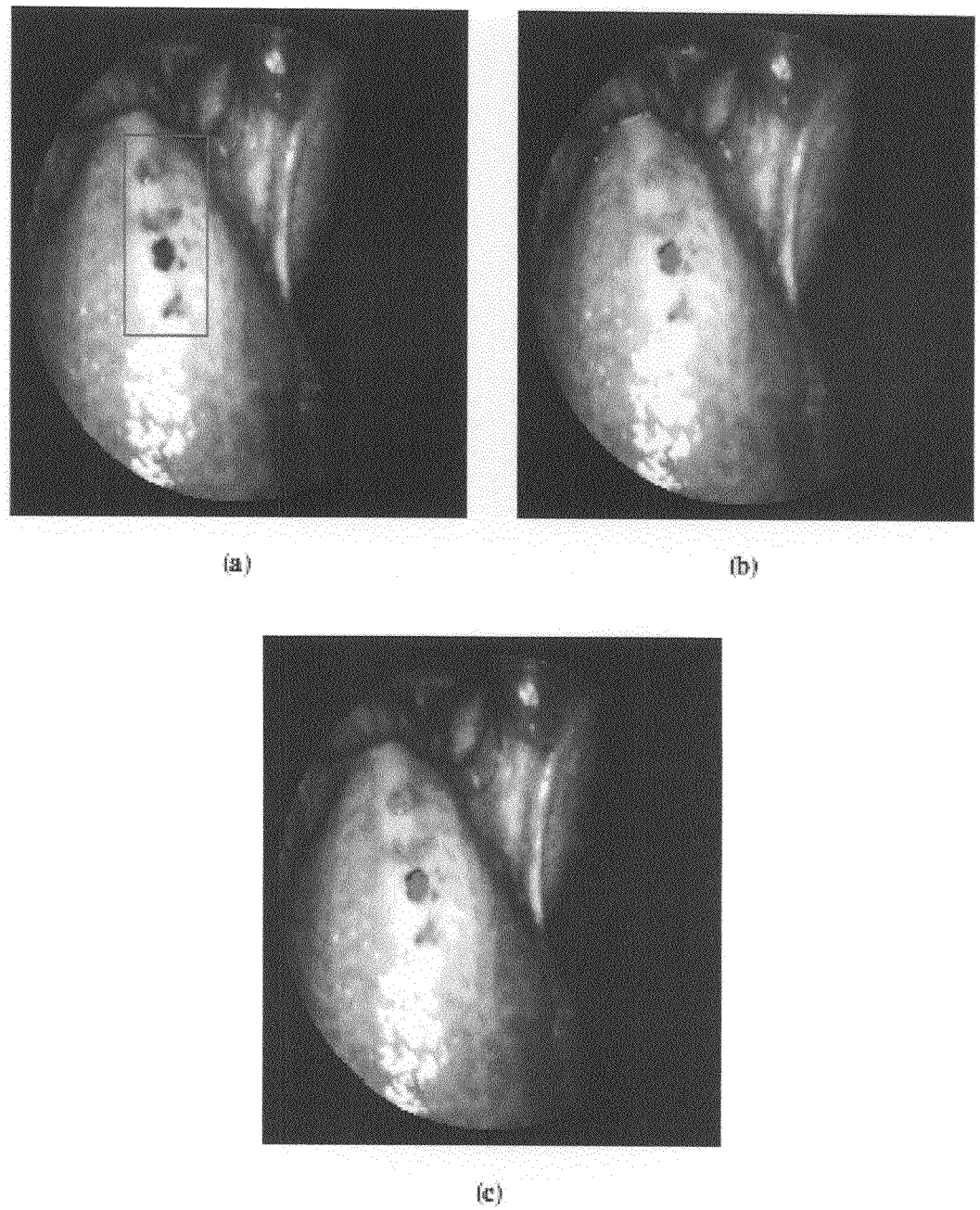
FIGS. 7a-7c are two port images of a chicken carcass taken by two port imaging system 10.

FIG. 7 shows one of the images of a chicken carcass taken by imaging system 10 and the detection results based on a band-ratio algorithm. Four types of contaminant materials, duodenum, cecum, colon, and ingesta, were manually deposited on the chicken carcass in approximately 89 mm$^2$, 144 mm$^2$, 127 mm$^2$, and 74 mm$^2$, respectively at the breast area. Background pixels with a reflectance of less than approximately 2.5% were masked out, and a ratio of the two images (approximately 560 nm/520 nm) was calculated. A threshold was then applied to the ratio of the two images to identify fecal and ingesta contaminants. Two thresholds, T=1.02 and T=1.10, were tested: T=1.02 was the greatest value that could be applied for detecting all contaminant locations (no false negative errors), and T=1.10 was the smallest value that produced no false positive errors. Red pixels in the images indicated contamination detected based on the thresholds, where the ratio of the two images was greater than the threshold. Overall, the result demonstrated that the four contaminated spots were successfully discriminated from the skin. However, several false-positive errors were observed in the T=1.02 image (FIG. 7c). The false-positives were improved by applying the greater threshold of approximately T=1.10. However, the T=1.10 threshold failed to detect some contaminants, especially duodenum, which could be detected by the smaller threshold, approximately T=1.02.

EXAMPLE 3

To test the new calibration algorithm for imaging system 50, a series of three-band images were collected to evaluate system's 50 calibration accuracy. With the imaging system fixed on an optical table, the distortion target was placed perpendicular to the optical axis of the imaging system 51 at four different distances with about 10 cm separation. Band images were taken at each distance and subsequently calibrated by the above described method for system 50. For evaluating the calibration accuracy, the image of port 1 and port 2 were used. The image misalignment error was calculated to be the offset of corresponding centroids of each dot between port 1 and port 2 images.

Figure 11:
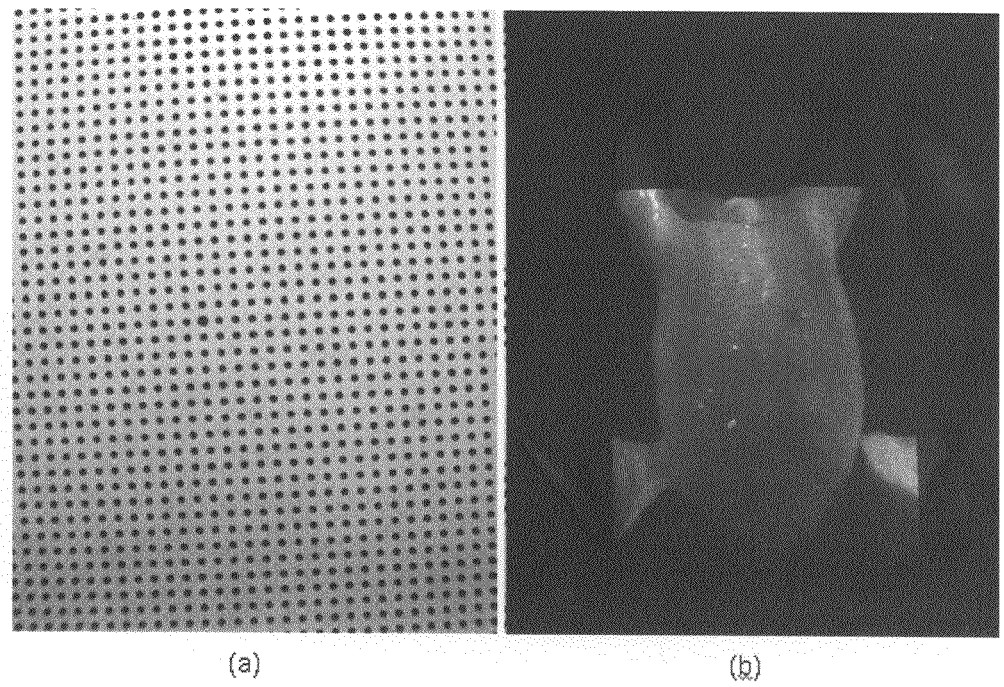
FIGS. 11a and 11b show images using calibration.

FIGS. 11a and 11b show the results of the system calibration. As a result of the system calibration, the band image was aligned accurately. FIG. 12a shows that the misalignment of the images of the distortion target, which was apparent in FIGS. 11a and 11b, was corrected; all dots were accurately aligned over two images. The average error over the image was approximately 5.03 µm (about 8.2 pixels). The test results are summarized in Table 4 below. Overall, very similar results were obtained at all distances tested; approximately 40 cm, 50 cm, 60 cm, and 70 cm. For the purpose of comparison, misalignment error without calibration was calculated as well. Without calibration, the average image misalignment error between port 1 and port 2 images was approximately 337.6 µm or about 26.17 pixels.

TABLE 5

Calibration Results.

| Distance (cm) | Average [µm] (pixel) | Max [µm], (pixel) |
| --- | --- | --- |
| 40 | 6.19 (0.48) | 12.64 (0.98) |
| 50 | 5.16 (0.40) | 12.9 (1.00) |
| 60 | 4.52 (0.35) | 12.13 (0.94) |
| 70 | 4.13 (0.32) | 13.55 (1.05) |
| Average | 5.03 (0.39) | 12.81 (0.99) |

EXAMPLE 4

To prove that system 50 calibration works on 3D objects, three band images were taken. FIG. 11(b) shows a composite image of three spectral bands: approximately 510 nm, 567 nm, and 800 nm and shows that the three band images are precisely aligned over the entire field of view with a 3D object being located in a short distance.

The foregoing detailed description is for the purpose of illustration. Such detail is solely for that purpose and those skilled in the art can make variations therein without departing from the spirit and scope of the invention.

| Listing of Elements | |
| --- | --- |
| 10. | Imagining System |
| 11. | Grip |
| 21. | Two-Port Camera System |
| 22a. | Monochrome CCD Camera |
| 22b. | Monochrome CCD Camera |
| 23. | Hub |
| 24. | Triggering Unit |
| 25. | Power Supply |
| 26. | Handheld PC |
| 27. | CCD Sensor |
| 30. | Optical System |
| 31. | Helicoid Barrels |
| 32. | Beamsplitter |
| 34. | Front lens Unit |
| 34a. | Positive achromatic lens |
| 34b. | Double concave lens |
| 36. | Bandpass filters |
| 36a. | Bandpass filter 520 nm |
| 36b. | Bandpass filter 560 nm |
| 37. | C-mount barrels |
| 38. | Rear Lens Unit |
| 38a. | Rear lens |
| 38b. | Rear lens |
| 39. | Aperature |
| 40. | Illumination System |
| 42. | DC lamp Housings |
| 44. | Power Supply |
| 45. | IEEE 1394A FireWire cable |
| 46. | LED Light |
| 48. | Heat Sink |
| 50. | Three Port Imaging System |
| 51. | Three Port Camera System |
| 51a. | Monochrome CCD Camera Port 0 |
| 51b. | Monochrome CCD Camera Port 1 |
| 51c. | Monochrome CCD Camera Port 2 |
| 52. | Cold Mirror |
| 54. | Spacer |
| 55a. | 35 mm Rear Lens Unit |
| 55b. | 35 mm Rear Lens Unit |
| 55c. | 35 mm Rear Lens Unit |
| 56. | C-Mount Ring retainer |
| 61a. | Visible Bandpass filter 800 nm |
| 61b. | Visible Bandpass filter 510 nm |
| 61c. | IR/NIR Bandpass filter |
| 62. | Front Lens Unit |

We claim:

1. A portable multispectral imaging system for determination of contamination of food comprising:
  a. at least two cameras with charge-coupled device sensors having at least two optical filters that are two bandpass filters, where a camera port 1 bandpass filter has a central wavelength of approximately 520 nm and a camera port 2 filter has a central wavelength of approximately 560 nm, and are capable of collecting at least two discrete narrow-band images,
  b. an illumination system in optical communication with said cameras,
  c. a front lens unit in optical communication with said at least two cameras,
  d. a beamsplitter in optical communication with said front lens and said two cameras, and
  e. at least two rear lens units in optical communication with said beamsplitter and said at least two cameras.

2. The system of claim 1 wherein in said illumination system includes ring-type light emitting diode lights encircling said front lens unit and a heat sink.

3. A portable multispectral imaging system for determinination of contamination of food comprising:

a. at least two cameras with charge-coupled device sensors wherein said at least two cameras is a system with three cameras designated port 0 camera, port 1 camera, and port 2 camera wherein said cameras have bandpass filters, port 0 camera filter is an IR/NIR bandpass filter, port 1 camera filter is a visible bandpass filter with a central wavelength of approximately 510 nm, and port 2 camera filter is a visible bandpass filter with a central wavelength of approximately 568 nm,
b. an illumination system in optical communication with said cameras,
c. a front lens unit in optical communication with said three cameras,
d. a beamsplitter in optical communication with said front lens and said three cameras, and
e. at least two rear lens units in optical communication with said beamsplitter and said at least three cameras.

4. The system of claim 3 further comprising a cold mirror in optical communication with port 0 and port 1 cameras and port 2 camera through a beamsplitter located between said cold mirror and port 2 camera.

5. The system of claim 3 wherein said rear lens units include 35 mm fixed focal, manual focus lenses.

* * * * *